(12) United States Patent
Kail, IV (10) Patent No.: US 6,940,403 B2
(45) Date of Patent: *Sep. 6, 2005

(54) REPROGRAMMABLE REMOTE SENSOR MONITORING SYSTEM

(75) Inventor: Karl A. Kail, IV, San Diego, CA (US)

(73) Assignee: CardioNet, Inc., San Diego, CA (US)

( * ) Notice: Subject to any disclaimer, the term of this patent is extended or adjusted under 35 U.S.C. 154(b) by 84 days.

This patent is subject to a terminal disclaimer.

(21) Appl. No.: 10/293,463

(22) Filed: Nov. 12, 2002

(65) Prior Publication Data

US 2003/0122677 A1 Jul. 3, 2003

Related U.S. Application Data (63) Continuation of application No. 09/829,601, filed on Apr. 9, 2001, which is a continuation of application No. 09/357,689, filed on Jul. 20, 1999, now Pat. No. 6,225,901, which is a continuation of application No. 08/813,846, filed on Mar. 7, 1997, now Pat. No. 5,959,529.

(51) Int. Cl.[7] .............................. G08B 1/08; A61N 1/37
(52) U.S. Cl. ........................... 340/539.12; 340/539.13; 340/539.19; 128/903; 702/19; 706/924; 607/60
(58) Field of Search ........................ 340/539.1, 539.12, 340/539.13, 539.19, 573.1, 10.51, 825.36, 825.49, 825.69, 825.72; 128/903, 904; 702/19; 706/911, 924; 607/17, 32, 60

(56) References Cited

U.S. PATENT DOCUMENTS

| | | | |
|---|---|---|---|
| 3,478,344 A | 11/1969 | Schwitzgebel et al. | ..... 340/312 |
| 3,768,014 A | 10/1973 | Smith et al | ...................... 23/2 |
| 3,885,552 A | 5/1975 | Kennedy | ............... 128/2.05 R |
| 3,902,478 A | 9/1975 | Konopasek et al | ..... 128/2.06 F |
| 3,925,762 A | 12/1975 | Keitlinger et al. | .......... 340/150 |

(Continued)

FOREIGN PATENT DOCUMENTS

| | | |
|---|---|---|
| DE | 4414 907 | 6/1995 |
| EP | 0 484 880 | 11/1991 |
| EP | 0 834 846 | 1/1996 |
| EP | 0 811 959 | 6/1997 |
| EP | 1 072 994 | 1/2001 |
| FR | 2 787 905 | 12/1998 |
| WO | WO 94/13197 | 6/1994 |
| WO | WO 96/25877 | 8/1996 |
| WO | WO 97/00708 | 1/1997 |
| WO | WO 99/44494 | 9/1999 |
| WO | WO 00/30529 | 6/2000 |
| WO | WO 00/62663 | 10/2000 |

*Primary Examiner*—Donnie L. Crosland
(74) *Attorney, Agent, or Firm*—Fish & Richardson P.C.

(57) ABSTRACT

An automated, real-time, reprogrammable monitoring and control system for portable, remote sensors and subjects includes one or more portable monitoring units, each of the portable monitoring units having a sensor, a location-determining device, and a sensor interface unit. Each sensor interface unit is separately configured to monitor its sensor and to transmit that sensor's data, via a digital wireless communications network, to a central monitoring device. The portable unit is carried or worn by a person or animal, or affixed to an inanimate subject.

23 Claims, 11 Drawing Sheets

U.S. PATENT DOCUMENTS

| | | | |
|---|---|---|---|
| 4,173,971 A | 11/1979 | Karz | 128/702 |
| 4,183,354 A | 1/1980 | Sibley et al. | 128/711 |
| 4,211,237 A | 7/1980 | Nagel | 128/698 |
| 4,230,127 A | 10/1980 | Larson | 128/706 |
| 4,241,237 A | 12/1980 | Paraskevakos et al. | 179/2 AM |
| 4,457,315 A | 7/1984 | Bennish | 128/704 |
| 4,531,527 A | 7/1985 | Reinhold, Jr. et al. | 128/696 |
| 4,535,783 A | 8/1985 | Marangoni | 128/711 |
| 4,598,272 A | 7/1986 | Cox | 340/539 |
| 4,651,157 A | 3/1987 | Gray et al. | 342/457 |
| 4,675,656 A | 6/1987 | Narcisse | 340/539 |
| 4,706,689 A | 11/1987 | Man | 128/903 |
| 4,742,357 A | 5/1988 | Rackley | 342/457 |
| 4,750,197 A | 6/1988 | Denekamp et al. | 379/58 |
| 4,777,478 A | 10/1988 | Hirsch et al. | 340/573 |
| 4,785,291 A | 11/1988 | Hawthorne | 340/573 |
| 4,819,860 A | 4/1989 | Hargrove et al. | 228/668 |
| 4,952,928 A | 8/1990 | Carroll et al. | 340/825.54 |
| 5,003,984 A | 4/1991 | Muraki et al. | 128/710 |
| 5,113,869 A | 5/1992 | Nappholz et al. | 128/696 |
| 5,172,698 A | 12/1992 | Stanko | 128/697 |
| 5,223,844 A | 6/1993 | Mansell et al. | 342/357 |
| 5,301,105 A | 4/1994 | Cummings, Jr. | 364/401 |
| 5,309,920 A | 5/1994 | Gallant et al. | 128/710 |
| 5,311,197 A | 5/1994 | Sorden et al. | 342/457 |
| 5,318,592 A | 6/1994 | Schaldach | 607/5 |
| 5,321,618 A | 6/1994 | Gessman | 364/413.06 |
| 5,334,974 A | 8/1994 | Simms et al. | 340/990 |
| 5,335,664 A | 8/1994 | Nagashima | 128/696 |
| 5,336,245 A | 8/1994 | Adams et al. | 607/32 |
| 5,348,008 A | 9/1994 | Bornn et al. | 128/642 |
| 5,389,934 A | 2/1995 | Kass | 342/357 |
| 5,394,879 A | 3/1995 | Gorman | 128/707 |
| 5,418,537 A | 5/1995 | Bird | 342/356 |
| 5,422,816 A | 6/1995 | Sprague et al. | 364/449 |
| 5,423,869 A | 6/1995 | Poore | 607/18 |
| 5,458,123 A | 10/1995 | Unger | 128/696 |
| 5,461,365 A | 10/1995 | Schlager et al. | 340/573 |
| 5,461,390 A | 10/1995 | Hoshen | 340/573.4 |
| 5,470,233 A | 11/1995 | Fruchterman et al. | 434/112 |
| 5,479,482 A | 12/1995 | Grimes | 379/59 |
| 5,487,755 A | 1/1996 | Snell et al. | 607/27 |
| 5,497,149 A | 3/1996 | Fast | 340/988 |
| 5,503,158 A | 4/1996 | Coppock et al. | 128/696 |
| 5,504,491 A | 4/1996 | Chapman | 342/357 |
| 5,515,419 A | 5/1996 | Sheffer | 379/58 |
| 5,522,396 A | 6/1996 | Langer et al. | 128/696 |
| 5,544,661 A | 8/1996 | Davis et al. | 128/700 |
| 5,549,113 A | 8/1996 | Halleck et al. | 128/671 |
| 5,564,429 A | 10/1996 | Bornn et al. | 128/696 |
| 5,565,858 A | 10/1996 | Guthrie | 340/10.33 |
| 5,568,814 A | 10/1996 | Gallant et al. | 128/672 |
| 5,573,506 A | 11/1996 | Vasko | 128/904 |
| 5,576,952 A | 11/1996 | Stutman et al. | 364/413.02 |
| 5,579,775 A | 12/1996 | Dempsey et al. | 128/670 |
| 5,617,871 A | 4/1997 | Burrows | 128/696 |
| 5,620,472 A | 4/1997 | Rahbari | 607/27 |
| 5,626,624 A | 5/1997 | Schaldach et al. | 607/24 |
| 5,626,630 A | 5/1997 | Markowitz et al. | 607/60 |
| 5,629,678 A | 5/1997 | Gargano | 340/573 |
| 5,649,303 A | 7/1997 | Hess et al. | 455/63 |
| 5,652,570 A | 7/1997 | Lepkofker | 340/573 |
| 5,678,562 A | 10/1997 | Sellers | 128/710 |
| 5,704,351 A | 1/1998 | Mortara et al. | 128/630 |
| 5,704,364 A | 1/1998 | Saltzstein et al. | 128/696 |
| 5,704,366 A | 1/1998 | Tacklind et al. | 128/716 |
| 5,713,856 A | 2/1998 | Eggers et al. | 604/65 |
| 5,720,770 A | 2/1998 | Nappholz et al. | 607/30 |
| 5,720,771 A | 2/1998 | Snell | 607/60 |
| 5,724,025 A | 3/1998 | Tavori | 340/573 |
| 5,729,197 A | 3/1998 | Cash | 340/539 |
| 5,730,143 A | 3/1998 | Schwarzberg | 128/710 |
| 5,731,757 A | 3/1998 | Layson, Jr. | 340/573 |
| 5,748,103 A | 5/1998 | Flach et al. | 340/870.07 |
| 5,749,367 A | 5/1998 | Gamlyn et al. | 128/696 |
| 5,749,907 A | 5/1998 | Mann | 607/27 |
| 5,752,976 A | 5/1998 | Duffin et al. | 607/32 |
| 5,759,199 A | 6/1998 | Snell et al. | 607/60 |
| 5,882,300 A | 3/1999 | Malinouskas et al. | 600/300 |
| 5,891,169 A | 4/1999 | Boheim et al. | 607/4 |
| 5,913,827 A | 6/1999 | Gorman | 600/509 |
| 5,913,881 A | 6/1999 | Benz et al. | 607/36 |
| 5,931,791 A | 8/1999 | Saltzstein et al. | 600/513 |
| 5,941,829 A | 8/1999 | Saltzstein et al. | 600/509 |
| 5,944,659 A | 8/1999 | Flach et al. | 600/300 |
| 5,950,110 A | 9/1999 | Hendrickson | 455/1 |
| 5,959,529 A | 9/1999 | Kail, IV | 340/539 |
| 5,964,794 A | 10/1999 | Bolz et al. | 607/121 |
| 5,966,692 A | 10/1999 | Langer et al. | 705/3 |
| 5,970,986 A | 10/1999 | Bolz et al. | 128/899 |
| 5,987,352 A | 11/1999 | Klein et al. | 600/509 |
| 5,987,519 A | 11/1999 | Peifer et al. | 709/230 |
| 6,026,008 A | 2/2000 | Feese | 365/63 |
| 6,038,469 A | 3/2000 | Karlsson et al. | 600/512 |
| 6,073,046 A | 6/2000 | Pael et al. | 600/509 |
| 6,083,248 A | 7/2000 | Thompson | 607/30 |
| 6,088,608 A | 7/2000 | Schulman et al. | 600/345 |
| 6,093,146 A | 7/2000 | Filangeri | 600/300 |
| 6,101,478 A | 8/2000 | Brown | 705/2 |
| 6,102,856 A | 8/2000 | Groff et al. | 600/301 |
| 6,154,674 A | 11/2000 | Meier | 607/23 |
| 6,160,478 A | 12/2000 | Jacobsen | 340/539 |
| 6,181,966 B1 | 1/2001 | Nigram | 607/4 |
| 6,192,274 B1 | 2/2001 | Worzewski | 607/14 |
| 6,225,901 B1 * | 5/2001 | Kail, IV | 340/539.11 |
| 6,245,092 B1 | 6/2001 | Schaldach | 607/1 |
| 6,263,243 B1 | 7/2001 | Lang | 607/17 |
| 6,466,793 B1 | 10/2002 | Wallstedt et al. | 455/450 |
| 2002/0143576 A1 | 10/2002 | Nolvak et al. | |

* cited by examiner

IF THE SIGNAL SOURCE IS A SENSOR OR INTERFACE TO A SENSOR, AND THE ACTIVITY REQUESTED IS DATA TRANSMISSION, THE COMMUNICATIONS DEVICE IS POWERED UP.

↓

WHEN THE COMMUNICATIONS DEVICE IS OPERATIONAL, A CONNECTION IS MADE TO THE CENTRAL MONITORING DEVICE (CMD).

↓

WHEN COMMUNICATION WITH CMD IS ESTABLISHED, THE PMU FORMATS AND TRANSMITS DATA RECEIVED FROM THE ACTIVE SENSOR(S) TO THE CMD.

↓

THE CMD RECEIVES, PROCESS AND STORES THE RECEIVED DATA IN A DATABASE ASSOCIATED WITH THE SENDING PMU.

↓

THE CMD OPERATOR IS NOTIFIED OF THE RECEPTION AND PROVIDED THE OPPORTUNITY TO DISPLAY THE RECEIVED DATA, ALONG WITH LOCALLY HELD REFERENCE INFORMATION, FOR REVIEW AND ACTION AS APPROPRIATE.

WHEN COMMUNICATION WITH THE CMD IS ESTABLISHED, THE FORMATTED MESSAGE IS SENT TO THE CMD.

THE PMU STOPS DATA TRANSMISSION UPON REACHING A CONDITION BASED ON MESSAGE TYPE, IS INSTRUCTED BY THE PMU OPERATOR, OR UPON LOSS OF THE COMMUNICATION LINK WITH THE CMD.

THE CMD RECEIVES, PROCESSES AND STORES THE RECEIVED DATA IN A DATABASE ASSOCIATED WITH THE SENDING PMU.

THE CMD OPERATOR IS NOTIFIED OF THE RECEPTION AND PROVIDED THE OPPORTUNITY TO DISPLAY THE RECEIVED DATA, ALONG WITH LOCALLY HELD REFERENCE INFORMATION, FOR REVIEW AND ACTION AS APPROPRIATE.

REPROGRAMMABLE REMOTE SENSOR MONITORING SYSTEM

This application is a continuation of application Ser. No. 09/829,601, filed on Apr. 9, 2001 which was a continuation of patent application Ser. No. 09/357,689, filed Jul. 20, 1999, now U.S. Pat. No. 6,225,901, for which priority is claimed; which in turn is a continuation of application Ser. No. 08/813,846, filed Mar. 7, 1997, now U.S. Pat. No. 5,959,529, for which priority is claimed.

BACKGROUND OF THE INVENTION

This invention relates to a portable, real-time, reprogrammable sensor monitoring system.

For over fifty years, governments have used both active and passive detection systems to track vehicles and troop movements. Intelligence communities have employed multi-million dollar satellite-based sensors including high-resolution cameras, infrared, and radio direction finding equipment to covertly monitor areas of interest. Only recently have the economies of scale and manufacturing breakthroughs permitted using derivatives of this technology for commercial applications.

Early commercial applications were satellite-based vehicle tracking systems using communications satellites in stationary (geosynchronous) orbits above the earth. These systems all employ terminal-antenna packages that are suitcase size and have healthy price tags, and consequently have been limited in use to large trucking firms. To reduce the price and terminal size for general consumer use, there have been two approaches. One employs wireless networks using low-earth orbiting satellites, and a second uses local cellular capabilities and other existing terrestrial wireless networks. With these new capabilities, the mobile asset monitoring and tracking market has grown to include all modes of surface transportation. The current major focus is in vehicle security and stolen vehicle recovery. The lower cost of communications has also permitted the market to expand into small fleet management, as well as navigation, traffic control, and roadside assistance.

Although these capabilities are valuable, the inventor has recognized that they do not address from a personal perspective a problem of increasing importance in society, which nearly everyone encounters during their lives. This problem is based upon the need to monitor a remotely located person or other subject that attempts to function normally but may or may be able to do so; and, if the subject does not function normally, notification must be made and corrective action taken. In a commonly encountered situation, an elderly or infirm relative attempts to lead a normal, independent life, but there is concern that, due to age or infirmity, the relative may not be able to do so. The concerned person may check from time-to-time by calling or visiting, but such checking may be unreliable because the relative may suddenly become ill long before the next check. Moreover, both the relative and the concerned person may be unable to recognize signs of impending distress. Too frequent a telephone call or visit may upset the relative.

There is a need for an approach that will allow a subject to function normally but be monitored and maintain communication as needed for abnormal or emergency situations. The present invention fulfills this need, and further provides related advantages.

SUMMARY OF THE INVENTION

The present invention provides an apparatus and a method for remotely monitoring the status of a living or an inanimate subject. The approach of the invention permits the monitoring of the condition and location of the subject, with interaction by the subject in some cases. The nature of the monitoring may be varied as necessitated by circumstances.

In accordance with the invention, an apparatus for remotely monitoring and assessing the status of a subject includes a portable monitoring unit comprising at least one automatic sensor associated with the subject, a portable-unit location-determining device; and a sensor interface unit. The sensor interface unit includes a programmable microprocessor having an active state and an inactive state. The microprocessor is operable to change from the inactive state to the active state responsive to the occurrence of any of a set of activating parameters for an activation condition including a preselected state of the at least one automatic sensor, a request signal from an external source, and, in the case of a human subject, a status signal by the subject. The microprocessor is in communication with the at least one automatic sensor and the location-determining device. The sensor interface unit further includes a communications device interface in communication with the microprocessor, a first transceiver of a communications device in communication with the communication device interface, and a power supply that provides power to the microprocessor, the communication device interface, and the first terminal of the communications device, as well as any other components of the portable unit that require power.

The one or more sensors are selected appropriately to the subject and the reasons for monitoring the subject. For example, the sensors could include an audio/visual sensor, a biological condition sensor, a chemical sensor, a meteorological sensor, a motion sensor, an electromagnetic sensor, a seismic sensor, or an apparatus sensor.

The location-determining device may either be selected to determine an absolute position of the portable monitoring unit or a relative position of the portable monitoring unit with respect to some other location. The location-determining device is preferably a global positioning system (GPS) receiver, but other types of devices such as triangulation devices or cellular-telephone-based devices may also be used.

Additionally, there is a central monitoring device including a second terminal of the communications device, and, desirably, a display in communication with the second terminal of the communications device and a computer that receives through the communications device and processes information from the sensor interface unit. The central monitoring device is typically able to maintain the necessary communications with a number of the portable monitoring units. The central monitoring device may be portable and may include its own location-determining capability for either an absolute position or a position relative to each portable monitoring unit.

In operation, the microprocessor is programmed with a set of activating parameters for the activation conditions and thereafter enters the inactive state. The microprocessor is activated responsive to the occurrence of the activating parameters of any of the activation conditions. The microprocessor obtains a status of the subject from the automatic sensor and the location of the portable unit from the location-determining device, and sends a status message, through the communications device, to the central monitoring device.

The microprocessor of the sensor interface unit is configured with a unique unit identifier, central monitoring device addressing data, and the initialization data and rules to be employed with each sensor embedded in or interfaced to the unit. The sensor interface unit may be configured on a sensor-by-sensor basis to transmit all sensor data received once activated, or all data meeting certain predefined criteria such as a time window, decibel level, or signal threshold. Data transmission from the sensor interface unit may be initiated manually, activated via a control signal from the central monitoring device, or automatically initiated in response to receipt of specified inputs from one or more of the interfaced sensors. In one embodiment, the sensor interface unit includes an audible tone or visible light generator feature that is activated by a call from the central monitoring device, and a means to activate/deactivate the feature.

The central monitoring device includes the second terminal of the communications device that permits it to communicate with any of a plurality of portable monitoring units, to uniquely identify each unit and the data relative to its configuration and use, to process the data received, and to display the processed data to an operator of the central monitoring device. The position data may be displayed on a map or referenced by distance and bearing relative to a known address or location. The central monitoring device includes the ability to forward the data received to other devices.

Thus, the present invention deals with events from the perspective of the subject being monitored. Events at the portable monitoring unit are sensed. The central monitoring device may make a periodic status query to the portable monitoring unit. The status inquiry may be made in an auto-response mode without the knowledge or participation of the subject, such as the periodic monitoring of sensors when the subject is sleeping or even when the subject is awake so as to be minimally intrusive. The portable monitoring unit may be configured to call in to the central monitoring device either periodically or responsive to pre-selected sensor readings. The status inquiry may also be made so as to require the response of the subject, for example to determine if an awake subject is mentally capable of responding. In the case of a human subject, the subject may also send a signal such as an "I'm OK" signal to the central monitoring device, either responsive to a page from the portable monitoring unit or upon the subject's own initiative. If the "I'm OK" signal is not received, the system determines the location of the portable monitoring unit, reviews available sensor data such as biological information or sensor information from a medical device used by the person, for example an infusion pump, and provides the information to the concerned person or, as appropriate, summons medical assistance.

A single central monitoring device may monitor a number of different portable monitoring units, each configured differently and reconfigurable as needed. An important feature of the invention is the ability to change (i.e., reprogram) the activating parameters and the functioning of the portable monitoring unit to varying needs. Some of the medical and status applications for human subjects were discussed in the preceding paragraph. The same device, but with different sensors, may be used to track and monitor inanimate objects such as valuable articles during shipment. In that case the sensors may indicate the condition of the article such as temperature, humidity, or movement, or associated equipment such as a refrigerator or heater.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
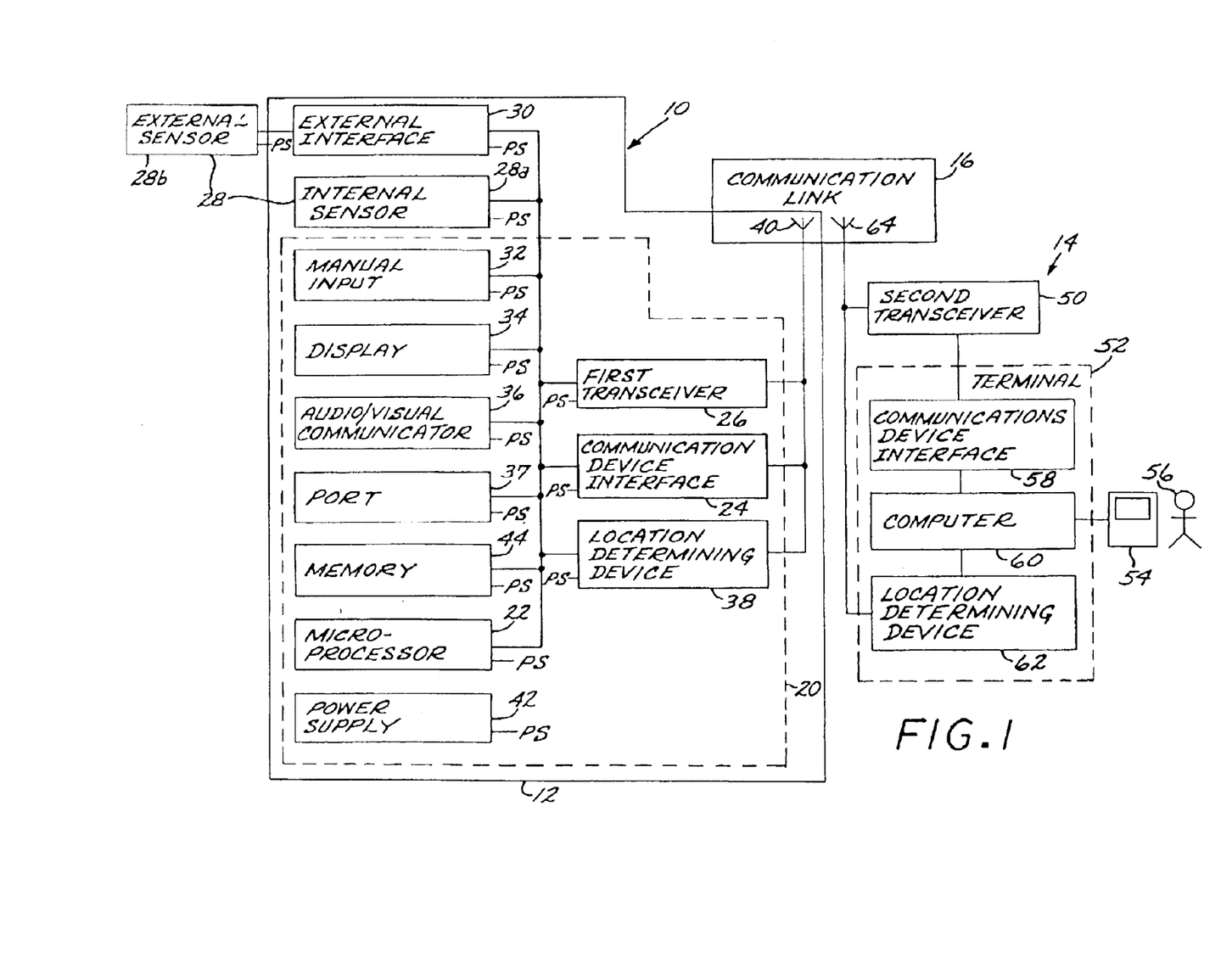
FIG. 1 is a block diagram of a preferred embodiment of an apparatus for remotely monitoring a subject.
Figure 2:
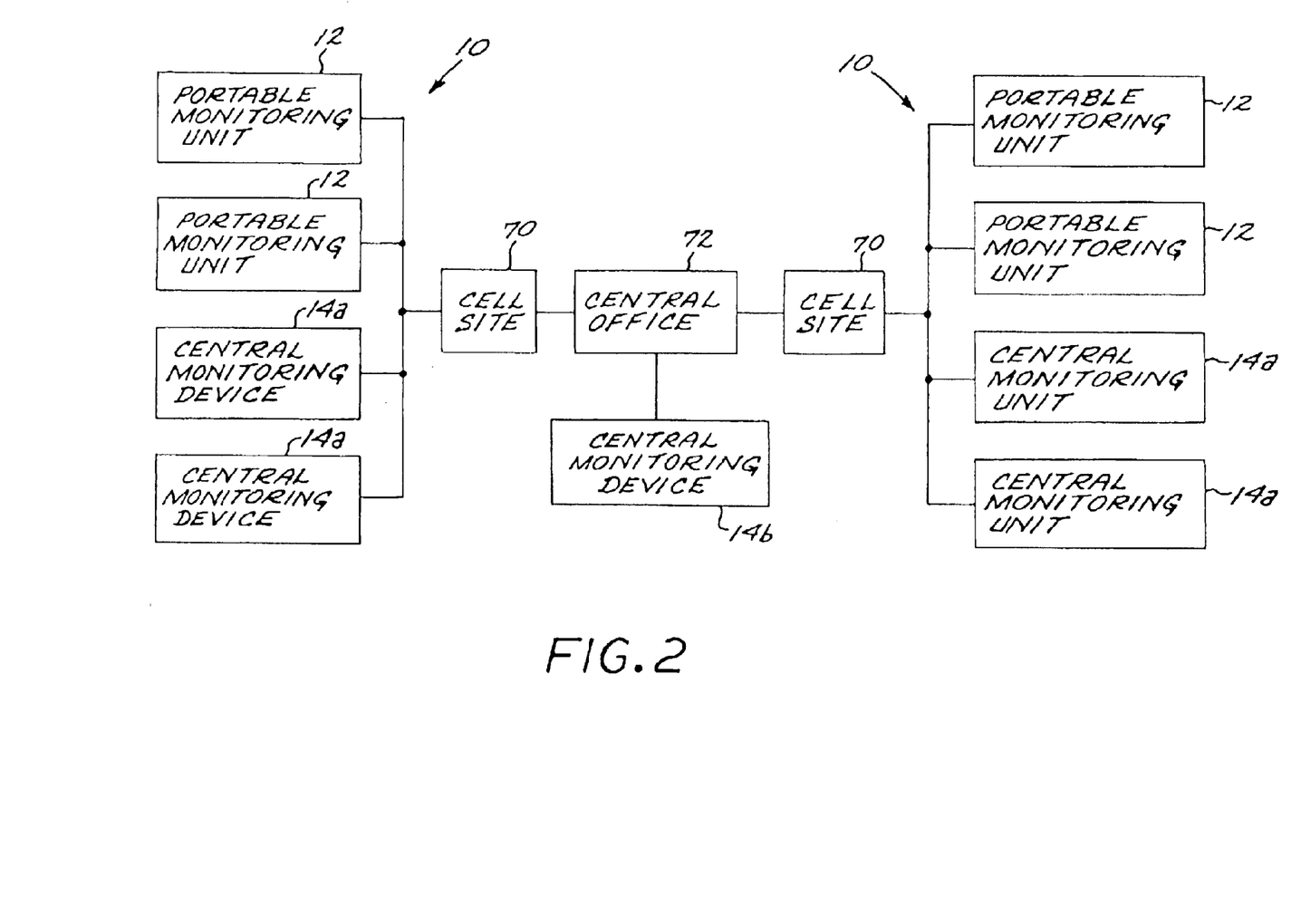
FIG. 2 is a block diagram of multiple-user architecture of the communications link of the present invention.

As shown in FIGS. 1 and 2, an apparatus 10 for remotely monitoring and assessing the status of a subject includes a portable monitoring unit 12 and a central monitoring device 14, which may communicate via a wireless communication link 16. FIG. 1 illustrates a preferred embodiment of the apparatus 10. FIG. 2 illustrates an architecture of the communications link wherein multiple portable monitoring units 12 and central monitoring devices 14 are accommodated.

The portable monitoring unit 12 includes a sensor interface unit 20 having a microprocessor 22 with multiple inputs and outputs, illustrated in a bus architecture. Communication of the microprocessor 22 with the wireless communication link 16, and thence with the central monitoring device 14, is effected through a communications device interface 24 and a first transceiver 26 of the wireless communication link 16. Information is gathered by one or more sensors 28. It is preferred that the wireless communication link 16 be a digital wireless communication link, but an analog link may be used instead. The sensors 28 may include internal sensors 28a embedded in the portable monitoring unit 12 and/or external sensors 28b that are connected to the portable monitoring unit through appropriate external interfaces 30. (In FIG. 1, the external interface 30 is illustrated as part of the portable monitoring unit 12, but it may be external to the portable monitoring unit.) The external sensors 28b may be any type that may be interfaced with the microprocessor 22 through the interface 30. For example, the interface 30 may be a standard serial or parallel interface, a PCMCIA interface, or an Ethernet interface. An external programming device or other device may also be connected to microprocessor 22 through the appropriate external interface 30.

An optional manual input device 32 communicating with the microprocessor 22 is accessible from the exterior of the portable monitoring unit 12, to allow a user or subject of the portable monitoring unit to provide information to the microprocessor 22. The manual input device 32 may be as simple as a switch such as a push button, or more complex such as a keypad. Optionally, a display 34, such as a liquid crystal display, and an audio and/or visual communicator 36, such as a tone generator, speaker, or flashing light, may be provided to signal the user of the portable monitoring unit 12 to take responsive action. An external port 37, such as a serial or a parallel communication port, is provided to permit information or reprogramming instructions to be input to the microprocessor 22 at the site of the portable monitoring unit 12. (A compatible sensor may also be connected through the external port 37.) The manual input device 32, the display 34, the audio and/or visual communicator 36, and external port 37 are each optional features that may be provided for specific applications.

The microprocessor 22 may be a Multi-Chip Package (MCP) such as the currently available Vadem VG330, the Advanced Micro Devices AMD Elan SC400, the NEC HHT-ASSP, or the ZF MicroSystems SMX/386. The microprocessor includes a power management unit which permits the microprocessor to be placed into an inactive state or awakened to an active state by a proper signal. The power management achieves conservation of the power of the power supply 42. The microprocessor is typically provided with memory 44, which may be a random access memory, a read-only memory, a mass storage device, or any combination of these types of memory. This memory may be shared with other components of the portable monitoring unit 12. The first transceiver 26 may be a single-board digital wireless module such as a WIT915 or WIT2500M marketed by Digital Wireless Corporation, with the appropriate interface 24. The first transceiver 26 has its own power management unit that permits the transceiver to be placed into an inactive state or awakened to an active state by a proper signal.

A location-determining device 38 is provided so that the location of the portable monitoring unit 12 may be determined. The location-determining device 38 is preferably a global positioning system (GPS) receiver having an antenna 40 shared with the antenna of the first transceiver 26. The GPS receiver may be a MicroTracker LP global positioning system receiver module available from Rockwell Semiconductor Systems. Other types of location-determining devices 38 such as those based upon cellula r cellsite position triangulations, LORAN, and the like, may also be used.

A power supply 42 such as a battery provides power for the components of the portable monitoring unit 12 requiring power, and optionally for the external sensor 28b and the external interface 30. In FIG. 1, the power connections between the powered components and the power supply 42 are indicated by "PS" to avoid the need for drawing the interconnections that would obscure the data-communications paths.

The central monitoring device 14 includes at least a second transceiver 50 of the wireless communication link 16, to establish communications between the first transceiver 26 of the portable monitoring unit 12 and the central monitoring device 14. Typically, the central monitoring device 14 further includes a terminal 52 having a communications device interface 58 to the second transceiver 50, and connections to a display 54 that may be viewed by an operator 56. The terminal 52 may be a simple manual system, or, preferably, it may be more complex as illustrated. In this more complex terminal 52, there is a computer 60 that communicates with the display 54 and communicates with and oversees the operations of the portable monitoring unit 12 in the manner to be discussed subsequently. The central monitoring device 14 may also be provided with a location-determining device 62, particularly if the central monitoring is movable or portable and its location must be determined. The location-determining device 62 has an antenna 64 shared with the antenna of the second transceiver 50. The location-determining devices 38 and 62 are typically selected to be compatible. If, for example, the location-determining device 38 is an autonomous GPS receiver, the location-determining device 62 normally is also a GPS receiver. On the other hand, the location-determining technique may utilize a triangulation, time-of-flight, or other type of measurement that requires coordination between the location-determining devices 38 and 62, which are then chosen with that technique in mind.

FIG. 2 illustrates an implementation of the apparatus 10 in an existing communications link and its integration with other similar units. In this case, the apparatus 10 is integrated into a cellular telephone communications system having multiple cell sites 70, here illustrated as two cell sites 70. The cell sites 70 are each in communication with a central office 72 (e.g., MTSO, or mobile telephone switching office), typically by land lines. Each cell site 70 may be in wireless communication with one or more portable monitoring units 12, here illustrated as two portable monitoring units. Each cell site 70 may be in wireless communication with one or more central monitoring devices 14. There are two types of such central monitoring devices illustrated, a central monitoring device 14a in wireless communication with the cell site 70, and a central monitoring device 14b in land-line communication with the cell site 70 through the central office 72. The central monitoring devices 14a would typically be mobile units, while the central monitoring device 14b would typically be a stationary unit. This architecture allows central monitoring devices 14 to be used in a wide variety of applications and to monitor many different portable units 12, of the same or different types and applications.

Where there are two or more of the portable monitoring units 12 whose operation is overseen by a single central monitoring device 14, as shown in FIG. 2, the central monitoring device assigns each of the portable monitoring units 12 with a unique identifier, to permit unambiguous communications with each of the units 12.

Figure 3:
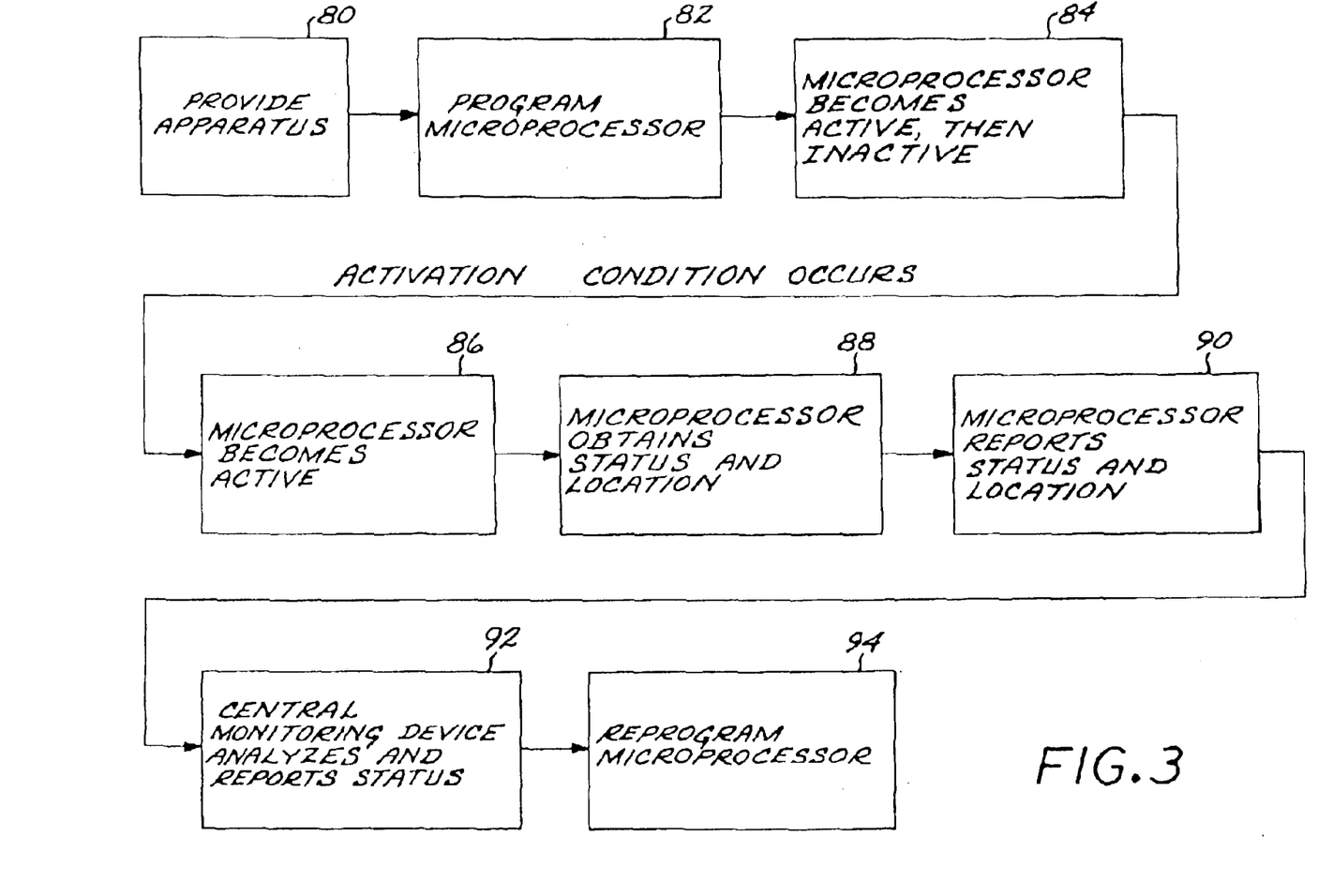
FIG. 3 is a block flow diagram of a preferred method for practicing the invention.

FIG. 3 illustrates the practice of the present invention. An operable apparatus is provided, numeral 80. The preferred apparatus is the apparatus 10 described previously. The microprocessor is programmed with a set of instructions for general operation and for activating parameters, numeral 82. The programming may be provided from the central monitoring device 14 or from a separate source connected through the port 37 or the external interface 30. The specifics of the programming will be discussed subsequently. The microprocessor first becomes active to check for the occurrence of any of the activating parameters of one of the activation conditions and, if none are present, becomes inactive, numeral 84. If any of the activating parameters are present, or upon occurrence of any of the activating parameters of one of the activation conditions, the microprocessor becomes (or remains) active, numeral 86. The microprocessor obtains the status of the subject and its location, numeral 88, and reports that information through the communication link 16 to the control monitoring device 14, numeral 90. The central monitoring device analyzes and reports the information, and takes action as appropriate, numeral 92.

At a later time, and as conditions may warrant, the microprocessor may be reprogrammed, numeral 94. The reprogramming may occur from the sources indicated above, either at the site of the portable monitoring unit or remotely from the central monitoring device through the wireless communication link 16.

Figure 4A:
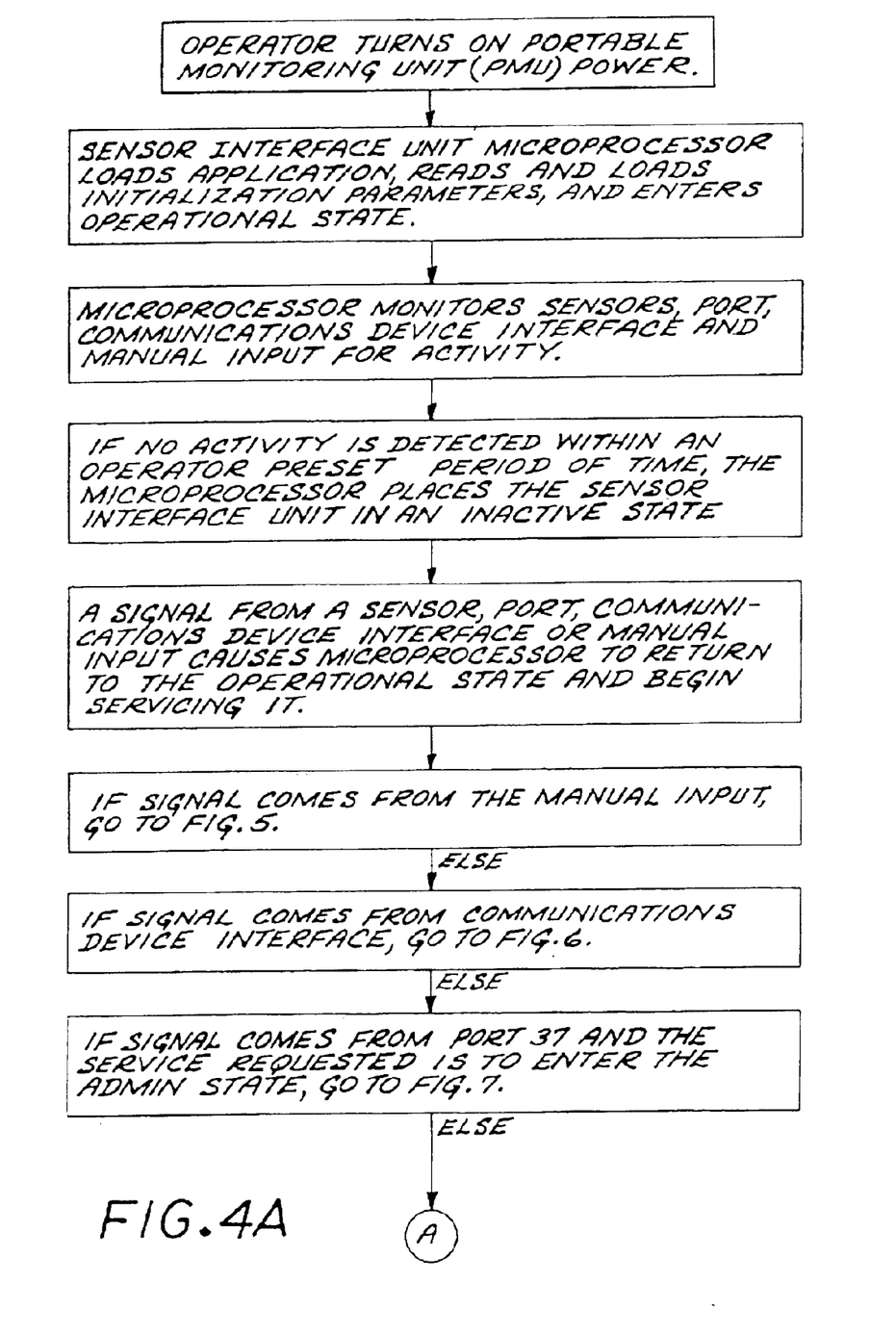
FIGS. 4–7 are block flow diagrams of the operation of the apparatus.
Figure 4B:
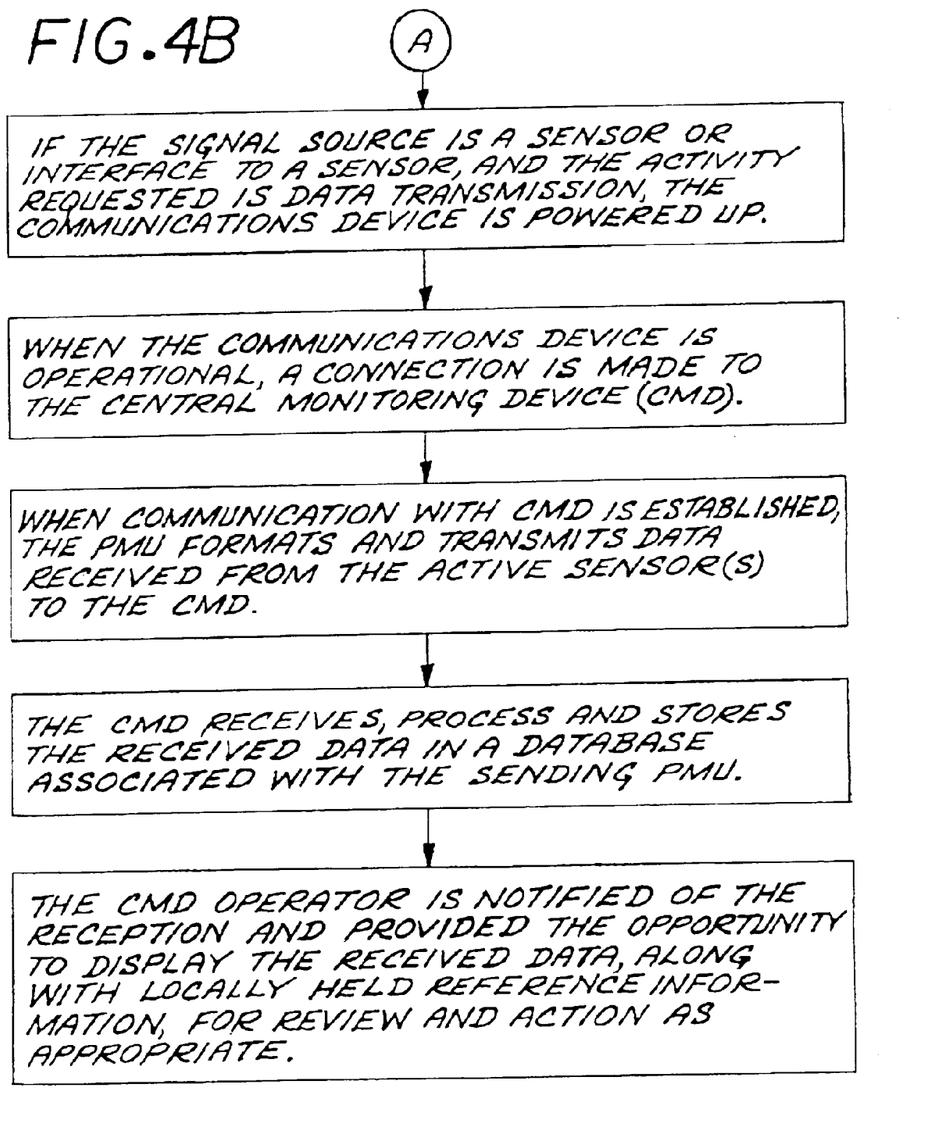
Figure 5A:
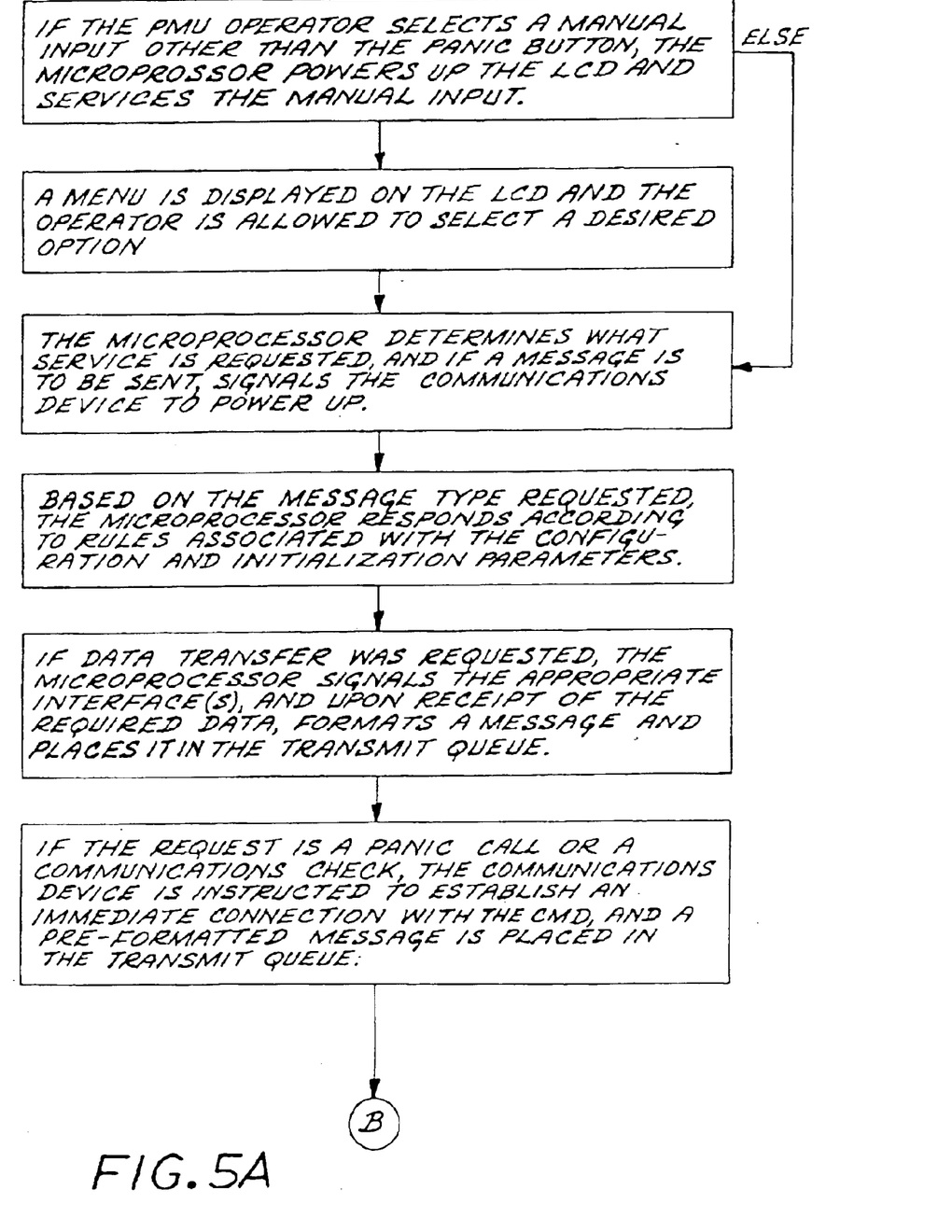
Figure 5B:
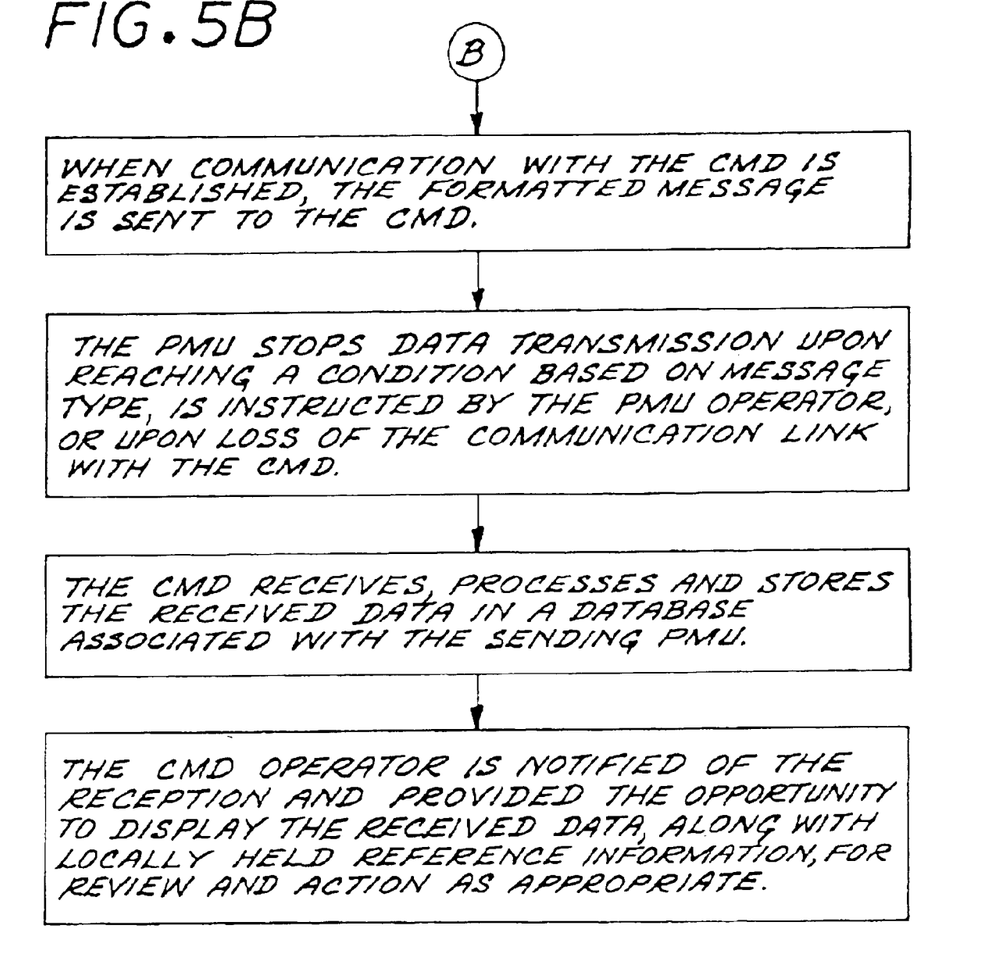
Figure 6A:
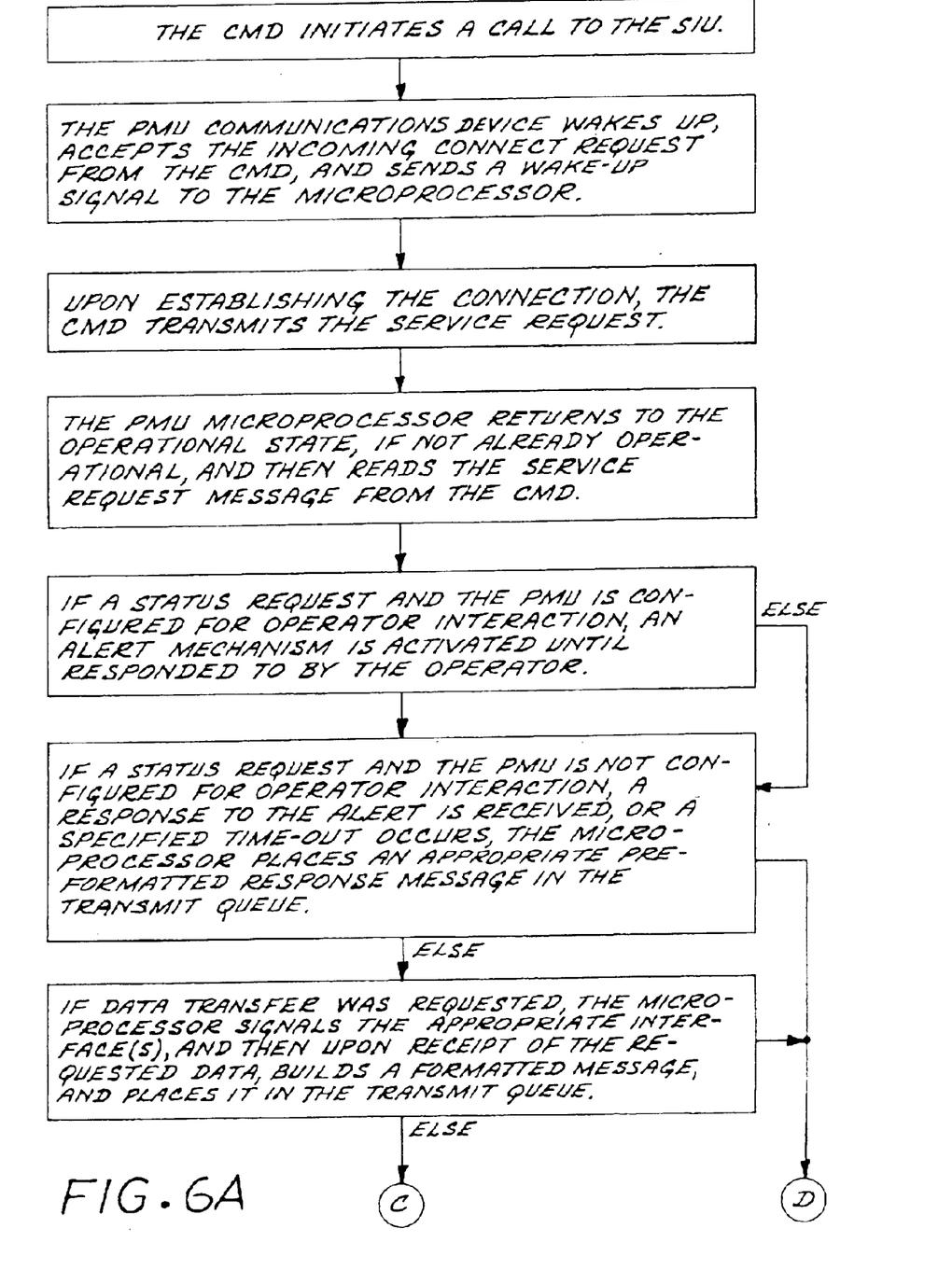
Figure 6B:
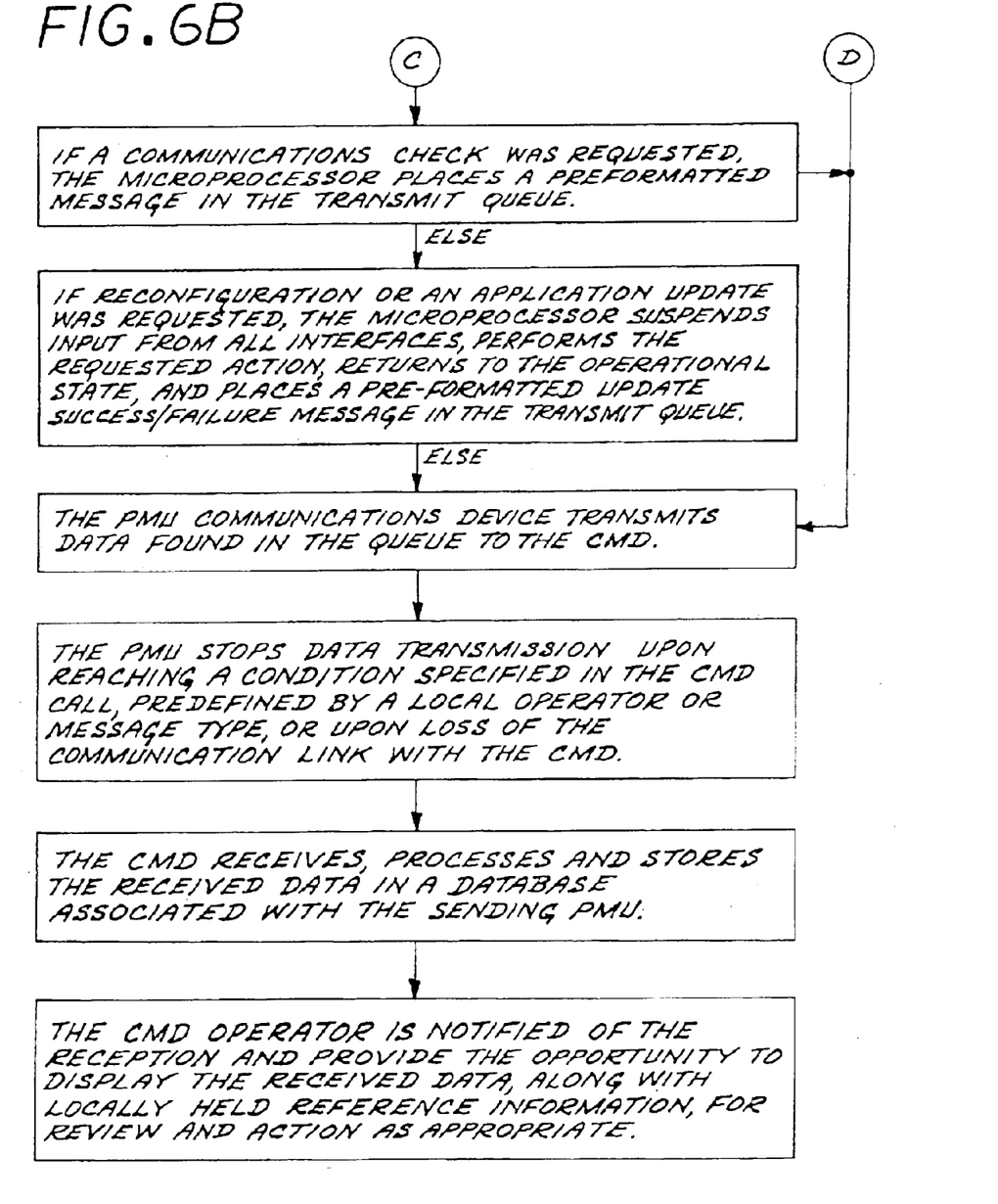
Figure 7A:
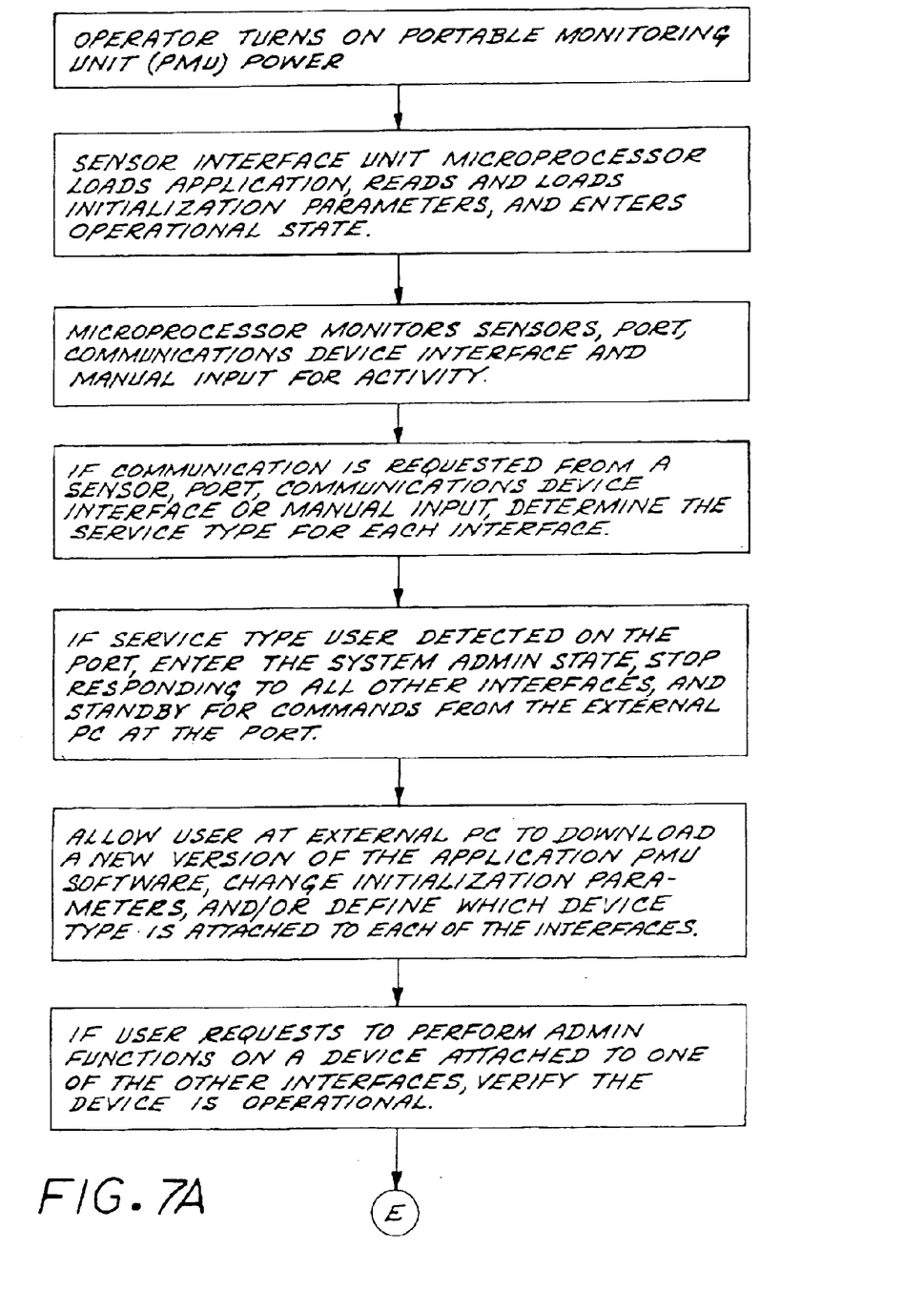
Figure 7B:
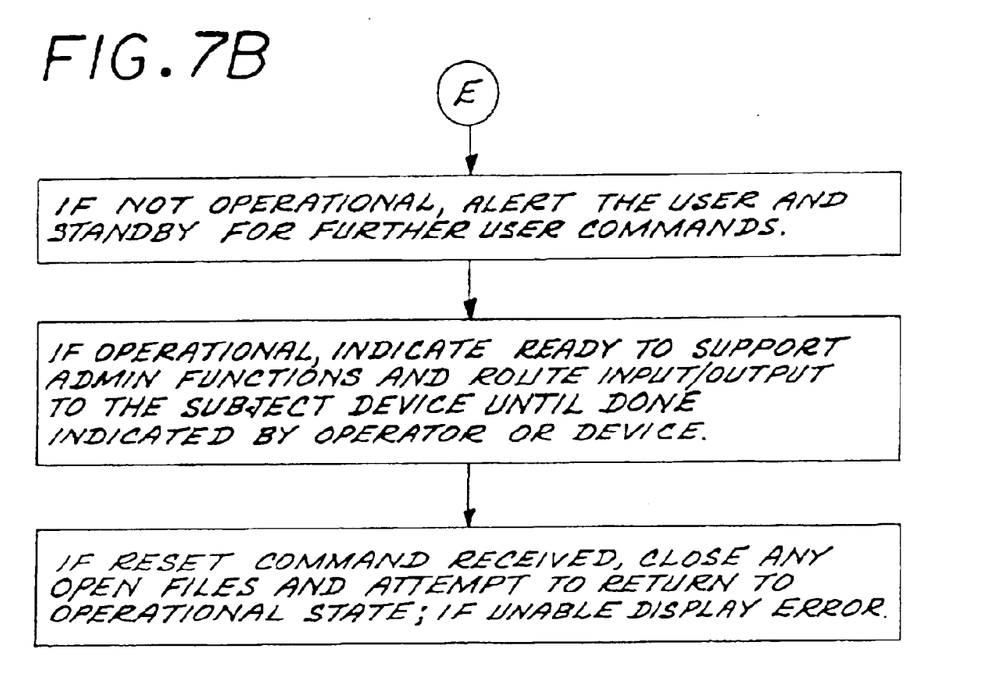

FIG. 4 illustrates the process flow associated with the preferred embodiment of the portable monitoring unit 12 for initialization of the sensor interface unit 20 upon being powered up, and then for formatting and sending data received from one or more sensors 28. Upon power-up, the microprocessor 22 loads the portable monitoring unit application from the non-volatile memory, loads the unit activation parameters from memory, and enters the active state. Once operational, the microprocessor reads the memory and then monitors the sensors 28, the port 37, the communications device interface 24, and the manual input 32 for activity. If there is no activity on the sensors 28, the port 37, or the manual input 32 for a period of time specified in the activation parameters, the microprocessor places the communications device interface 24 into an inactive state. A signal from any of the sensors 28, the port 37, the communication device interface 24, or the manual input 32 causes the microprocessor to return to the active state. If the signal comes from the manual input 32, the process described in relation to FIG. 5 is followed; if the signal comes from the communication device interface 24, the process described in relation to FIG. 6 is followed. If the signal comes from the port 37 and the service requested is to enter the administration state, the process described in FIG. 7 is followed. If the signaling source is the sensors 28 or the port 37 interfaced to a sensor, and the activity requested is data transmission to the control monitoring device 14, the first transceiver 26 is powered. When the first transceiver 26 is powered, a connection is established with the central monitoring device 14 via the communications link 16. The microprocessor 22 formats the data received from the sensor 28 and transmits it to the central monitoring device 14. Upon receipt, the central monitoring device 14 processes and stores the received data in a database associated with the sending portable monitoring unit 12. The operator 56 is notified of the data reception and provided the opportunity to display the data, along with locally stored reference information pertaining to the sending portable monitoring unit 12 for review and action as appropriate.

FIG. 5 describes the process flow when the subject desires to initiate a transmission to the central monitoring device 14 from the manual input device 32 of a particular portable monitoring unit 12. Depending upon the type of manual input device, the communication may be direct (e.g., a panic button signal) or may involve use of the display 34 as well. In the latter case, the microprocessor 22 activates the display 34 and presents a menu for the subject. The subject selects options from the menu. The microprocessor determines the service requested and the message to be sent, and powers the first transceiver 26. The microprocessor determines what action is to be taken from the message type requested and the rules associated with the current configuration and the activation parameters. If a data transfer is requested, the microprocessor determines for each applicable interface the action required, based upon the configuration of the sensor interface unit 20 and the activation parameters. As required, the microprocessor actuates the interfaced device and sends a service request to it. The microprocessor reads the data buffer associated with each applicable interface, and upon receipt of the required data, prepares a formatted message and places the message in the queue for the first transceiver 26. If the request is a panic call or a communications check, an immediate connection is established with the central monitoring device, and a pre-formatted message is placed in the transmit queue. When the first transceiver becomes operational, a connection is established with the central monitoring device 14 via the communications link 16. When the connection is established with the central monitoring device 14, the communications device interface 24 reads the transmit queue and transmits all available messages to the central monitoring device 14. Upon receipt, the central monitoring device processes the received message and stores the data in a database associated with the sending portable monitoring unit 12. The operator 56 is notified of the data reception and provided the opportunity to display the data, along with locally stored reference information pertaining to the sending portable monitoring unit 12 for review and action as appropriate.

FIG. 6 illustrates the process when the operator 56 or the terminal 52 desires to query a specific portable monitoring unit 12, to monitor one or more of the sensors 28, to send a message to the subject through the portable monitoring unit 12, or to change the microprocessor's configuration or applications software. A call is initiated by the operator or the terminal via the communications link 16. The connect request is detected by a low-current receiver within the first transceiver 26, and it is turn activates the full first transceiver 26 and sends an activation signal to the microprocessor 22. Once activated, the microprocessor acknowledges the call. The central monitoring device 14 then forwards the service request message to the portable monitoring unit 12 and thence to the microprocessor and its memory 44. If a status request for a response by the subject is made, the display 34 or the audio/visual communicator is operated until the subject responds through the manual input 32. If the sensor interface unit is not configured properly when the request for response by the subject is made, a timeout occurs so that the configuration can be accomplished. If the call instead requested data from one of the sensors 28, the microprocessor signals the sensor. Upon receipt of the requested data from the sensor, a formatted message containing the data is prepared and transmitted. If reconfiguration (i.e., reprogramming) is requested, the microprocessor suspends all other input, places a message that an update is in progress on the display 34, receives the transmitted updating information, performs the requested action, returns to the operational state, places an update success/failure message into the transmit queue, and displays the results on the display 34. The status of the update is transmitted to the central monitoring device 14. The operator 56 is notified of the data reception and provided the opportunity to display the data, along with locally stored reference information pertaining to the sending portable monitoring unit 12 for review and action as appropriate.

In some cases, it is desired to receive either data or reprogramming from an external source such as a personal computer connected to the portable monitoring device 12 through the port 37. If the port 37 is interfaced to an external sensor and the information is data, the reading is performed in the same manner as described in relation to FIG. 4 for the sensors 28. If the information is reprogramming in the form of an application update or new parameters, the portable monitoring unit 12 is powered in the normal manner. The original application loads into the microprocessor 22, the activation parameters are retrieved and set, and the sensor interface unit 20 enters the operational state. However, if reprogramming is to be loaded through the port 37, no input is accepted through any other interface. The external source loads the reprogramming through the port 37. This reprogramming may be either an entire new applications program or new parameters for the existing program. If the operator requests to perform an administration function on a device attached to one of the other interfaces, the microprocessor first verifies that the device is operational. If the device is not operational, the microprocessor alerts the operation and stands by for further commands. If the device is operational, the microprocessor indicates that it is ready to support the administration functions and begins routing input and output to the device until the operation or the device signals it to stop. If a Reset command is received, the microprocessor closes any open files and attempts to return to the operational state. If it is unable to return to the operational state, an error message is displayed.

The procedures set forth in FIGS. 4-7 provide the building blocks by which a wide variety of queries, status checks, and reprogramming may be accomplished. For example, the central monitoring device can periodically monitor the sensors 28 to determine the status of the subject. The subject may be required to "report" by operating the manual input periodically to demonstrate a satisfactory mental condition. If the subject fails to report, then the control monitoring device can initiate a call, activate the audio-visual communicator 36 and/or the display 34 until the subject responds, and then require the subject to perform a series of input responses through the manual input 32 to demonstrate a satisfactory mental condition. If either the sensor information or the manual input of the subject is not satisfactory, the control monitoring device 14 can report this fact and the apparent nature of the problem to the concerned person or summon help. The location of the subject is available to the concerned person or emergency responders from the location-determining device 38, whose data is automatically communicated to the central monitoring device as part of the message information. As will be apparent, many different types of these procedures may be used and reprogrammed into the portable monitoring unit 12.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. Apparatus for remotely monitoring and assessing the status of a human subject, the apparatus comprising:
   at least one automatic sensor associated with and monitoring the condition of the human subject; and
   a portable monitoring unit capable of communicating with a central monitoring device, the portable monitoring unit comprising:
      a programmable microprocessor in communication with the at least one automatic sensor, the microprocessor being responsive to the occurrence of any of a set of activating parameters, the activating parameters selected from the group consisting of a preselected state of the at least one automatic sensor and a request signal from an external source,
      a first transceiver in communication with the microprocessor, for communicating signals between the microprocessor and the central monitoring device, and
      a power supply connected to provide power to at least one of the microprocessor and the first transceiver.

2. The apparatus of claim 1, wherein at least one automatic sensor comprises a sensor selected from the group consisting of a biological condition sensor, an accelerometer, and an audio sensor.

3. The apparatus of claim 1, wherein the portable monitoring unit further comprises:
   a portable-unit location-determining device.

4. The apparatus of claim 1, wherein the programmable microprocessor has an active state and an inactive state, the microprocessor being operable to change from the inactive state to the active state responsive to the occurrence of any of the activating parameters.

5. The apparatus of claim 1, further comprising:
   at least one monitoring device in communication with the central monitoring device.

6. The apparatus of claim 1, wherein the portable monitoring unit comprises
   an audio/visual indicator in communication with the microprocessor.

7. The apparatus of claim 1, wherein the portable monitoring unit comprises
   a subject status signal input device activatable by the human subject and in communication with the microprocessor.

8. The apparatus of claim 1, further comprising a portable central monitoring device.

9. The apparatus of claim 1, further comprising:
   at least one additional portable monitoring unit having the same structure as the portable monitoring unit.

10. The apparatus of claim 1, wherein the request signal from the external source comprises a periodic status query from the central monitoring device.

11. The apparatus of claim 1, wherein the preselected state of the at least one automatic sensor comprises a preselected sensor reading from a medical device.

12. The apparatus of claim 1, wherein the microprocessor is responsive to receive a reprogrammed activating parameter.

13. The apparatus of claim 1, wherein the microprocessor is responsive to transmit all data received once activated.

14. The apparatus of claim 1, wherein the microprocessor is responsive to transmit data meeting a certain predefined criteria.

15. A method for remotely monitoring the status of a human subject, the method comprising:
   providing the human subject with at least one automatic sensor selected from the group consisting of a biological condition sensor, a medical device, and an audio sensor;
   providing the human subject with a portable monitoring unit comprising:
      a programmable microprocessor in communication with at least one automatic sensor,
      a first transceiver in communication with the microprocessor, and
      a power supply to provide power to at least one of the microprocessor and the first transceiver;
   programming the microprocessor with a set of activating parameters for one or more activation conditions;
   the microprocessor obtaining a status of the human subject from the at least one automatic sensor; and
   the microprocessor sending a status message over the first transceiver, the status message comprising information relating to the status of the human subject.

16. A method for remotely monitoring the status of a human subject, the method comprising:
   providing the human subject with a portable monitoring unit comprising:
      a programmable microprocessor,
      a first transceiver in communication with the programmable microprocessor,
      a communications device interface to communicate between the programmable microprocessor and the first transceiver, and
      a power supply to provide power to at least one of the microprocessor, the communication device interface, and the first transceiver;
   programming the microprocessor with a first set of operating instructions;
   receiving information relating to the operation of the microprocessor using the first set of operating instructions; and
   reprogramming the microprocessor using information transmitted through the first transceiver with a second set of operating instructions.

17. A method for remotely monitoring the status of a human subject, comprising:

providing the human subject with at least one automatic sensor;

providing the human subject with a portable monitoring unit comprising:
- a portable-unit location-determining device,
- a programmable microprocessor in communication with at least one automatic sensor and the location-determining device,
- a communication device interface in communication with the programmable microprocessor,
- a first transceiver of a communications device in communication with the communication device interface, and
- a power supply to provide power to the microprocessor and the first transceiver; and monitoring the human subject with the portable monitoring unit and the at least one automatic sensor, wherein monitoring comprises:

requesting a report from the human subject, and reporting the status and location of the human subject in the event of an unsatisfactory response from the human subject to the request.

18. The method of claim 17, further comprising:

receiving a voice communication from the central monitoring device.

19. A method comprising:

receiving a set of activating parameters, at least one activating parameter relating to sensor readings to be received from a biological condition sensor;

receiving sensor readings relating to the biological condition of a human subject from the biological condition sensor;

changing to an active state based on the at least one activating parameter and the biological condition of the human subject; and sending a message over a transceiver of a communications device to a central monitoring service, the status message including information relating to the biological condition of the human subject.

20. The method of claim 19, further comprising:

identifying the biological condition of the human subject using the set of activating parameters.

21. The method of claim 19, further comprising:

receiving a second set of activating parameters; and reprogramming the microprocessor using the second set of activating parameters.

22. The method of claim 21, wherein the microprocessor is remotely reprogrammed.

23. The method of claim 19, wherein receiving the set of activating parameters comprises:

receiving an activating parameter relating to a request signal from an external source.

* * * * *